United States Patent [19]

Grunstein

[11] Patent Number: 4,802,492
[45] Date of Patent: Feb. 7, 1989

[54] METHOD FOR DETERMINING RESPIRATORY FUNCTION

[75] Inventor: Michael M. Grunstein, Denver, Colo.

[73] Assignee: National Jewish Center for Immunology and Respiratory Medicine, Denver, Colo.

[21] Appl. No.: 24,684

[22] Filed: Mar. 11, 1987

[51] Int. Cl.$^4$ ............................................. A61B 5/08
[52] U.S. Cl. .................................................... 128/720
[58] Field of Search ..................... 128/720, 716, 725

[56] References Cited

U.S. PATENT DOCUMENTS

4,031,885 6/1977 Davis et al. ........................ 128/720
4,036,222 7/1977 Gillard et al. ...................... 128/720
4,259,967 4/1981 Vooren et al. ..................... 128/720

Primary Examiner—Lee S. Cohen
Attorney, Agent, or Firm—Felfe & Lynch

[57] ABSTRACT

A method for determining respiratory function in subjects, as well as the apparatus thus employed. The method involves blocking exhalation while the subject inhales spontaneously. Increased volume in the lungs and face mask pressure are measured to determine respiratory compliance. When the exhalation block or occlusion is removed, flow of exhaled air and volume changes in the lungs are measured to determine the time constant. The relationship between time constant and respiratory compliance permits determination of respiratory resistance.

10 Claims, 6 Drawing Sheets

METHOD FOR DETERMINING RESPIRATORY FUNCTION

FIELD OF THE INVENTION

This invention relates to a method for measuring respiratory function in an individual, as well as the apparatus used in such determination. The method is especially useful for measuring respiratory function in individuals who are not able to give meaningful objective information during standard respiratory evaluation tests, such as infants, the seriously ill, the infirm, and so forth.

BACKGROUND AND PRIOR ART

The measurement of various respiratory parameters, such as resistance to air flow through bronchial tracts, elastance of pulmonary tissue, and so forth, is essential in the diagnosis of many pathological respiratory conditions, whether these are chronic or temporary.

Medical science uses many different methods for determination of respiratory parameters, some of which are disclosed in the patent literature. For example, U.S. Pat. No. 4,036,222 teaches an apparatus for continuous measurement of the resistance and elastance referred to supra. These are continuously monitored and displayed, and show respiratory air flow and endothoracic pressure variations in the subject.

U.S. Pat. No. 4,031,885 teaches measurement of some different values, i.e., lung pressure and compliance, as well as resistance. The apparatus disclosed therein is used in connection with a respirator system. Compliance and resistance are determined by measuring the pressure of the respirator system at the end of patient inspiration and at the end of plateau phase. The measurements are related to the volume of gas delivered to the patient, and then computing compliance and resistance from the volume, pressure, and time differential values, using known equations relating these values.

U.S. Pat. No. 4,259,967, describes an apparatus useful in measuring respiratory resistance. The apparatus contains a closable valve which permits or blocks passage of exhaled air from the subject. The passageway through which the exhaled air passes also contains means for measuring the rate of flow, or pressure, of exhaled air. There is no way, however, for relating the measured pressure to the volume of air exhaled, and hence no way of determining whether there is a diseased state in the subject's respiratory system, when the disease is characterized by particular relationships between inhaled volume and exhaled pressure.

SUMMARY OF THE INVENTION

Disclosed herein is a method for measuring respiratory function in a subject, as well as apparatus for use in said method. The method involves covering the nose and mouth of a subject with a leak-free, sealable facemask means. The facemask means is attached in series to a flowmeter, or pneumotochograph and a two way valve means which permits the subject to inhale air via one part and exhale air via the other. The exhalation part is equipped with occlusion means, which are controllable by the investigator, technician, physician, etc. Additionally, there is provided a means which is attached to the facemask and a pressure transducer, which means permits continuous measurement of the airway or mask pressure continuously.

In practice, the subject is allowed to breathe spontaneously while the exhalation port is occluded for a defined period, generally 3–5 breaths. This occlusion results in progressive cumulation of air in the lungs after each successive inhalation. During the subject's breathing, the cumulative increases in the volume of air introduced to the lungs and increases in mask pressure are measured. These parameters are related to each other in a manner described infra, which permits one to determine compliance of the subject's respiratory system. When occlusion of the exhalation port is released, the flow of exhaled air is measured, and this is related to the corresponding change in exhaled volume in the subject's lungs. Exhaled flow and volume are used to determine the time constant of the subject's respiratory system. The time constant, once determined, is used together with the compliance measurement to determine the resistance of the subject's respiratory system. This provides a way for determining the relative health or disease of the subject with respect to abnormalities in, e.g., airflow resistance as occurs in conditions such as asthma, chronic obstructive pulmonary disease, etc., and parenchymal lung stiffness, as occurs in conditions such as emphysema, restructive lung diseases, etc.

How these and other aspects of the invention are achieved will be explained in the disclosure which follows.

BRIEF DESCRIPTION OF THE FIGURES

FIG 1 is a graphic representation of an example of the invention. A tracing of volume, airflow, and air pressure is given for a case where expiratory occlusion was applied for 3 respirations and released during the fourth.

DETAILED DESCRIPTION OF PREFERRED EMBODIMENTS

A study was conducted on 22 infants comprising three groups (1) 8 full-term normals; (2) 7-pre-term infants with chronic lung disease (CLD), all of which required transient mechanical ventilation following birth due to the presence of neonatal respiratory disease syndrome and, subsequently, remained oxygen dependent; and 3) 7 term infants with reversible obstructive airway disease (ROAD), evidenced by a history or intermittent wheezing acutely improved following inhaled bronchodilator therapy. The subjects were clinically stable at the time of study, and all of the infants with CLD required continuous supplemental oxygen delivered by low blow-by blow via nasal cannula (i.e., <1L/min). With the exception of three infants, all the patients with CLD and ROAD received their routine inhaled bronchodilator therapy at least three hours prior to study. The infants were studied approximately one hour following their last feeding, and within one hour of sedation with chloral hydrate (50-100 mg/kg body wt., orally). All the subjects were studied after informed consent was obtained from one or both parents.

With the sleeping infant in the supine position, a firm rubber mask was placed over the nose and mouth, and a tight leak-free seal was maintained with silicone putty placed around the rim of the face mask. Airflow was monitored via a Fleisch pneumotachograph (type "1" or "2") which was connected by still tubing to a Validyne MP-45 differential pressure transducer (±2 cm $H_2O$) having a frequency response that was flat up to 30 Hz. One end of the pneumotachograph was fitted to the face mask, while the other was connected to a two-way valve system having separate inspiratory and expiratory ports. The resistance of the added equipment was less than 0.0025 cm $H_2O/ml^{-1}$/sec, and virtually linear up to flow rates of 500 ml $sec^{-1}$. Mask pressure was monitored using a Validyne (±100 cm $H_2O$) differential pressure transducer which was attached by via stiff tubing to a port within the valve system, interposed between the inspiratory and expiratory valves. The flow signal was electronically integrated to volume, with the 95% response time of the integrator to a test square wave input of 5 volts being less than 5ms. The volume, flow and mask pressure signals were continuously monitored on a multi-channel recorder, as well as on a tape recorder. Moreover, the flow-volume loops were displayed on a storage oscilloscope, and subsequently photographed with a camera. Finally, arterial oxygen saturation ($SaO_2$) was also continuously monitored using an ear oximeter. In all the subjects with CLD, prior to each expiratory volume clamp maneuver (described infra), supplemental oxygen was delivered via the inspiratory port of the two-way valve system to avoid any significant decreases in $SaO_2$.

Figure 1:
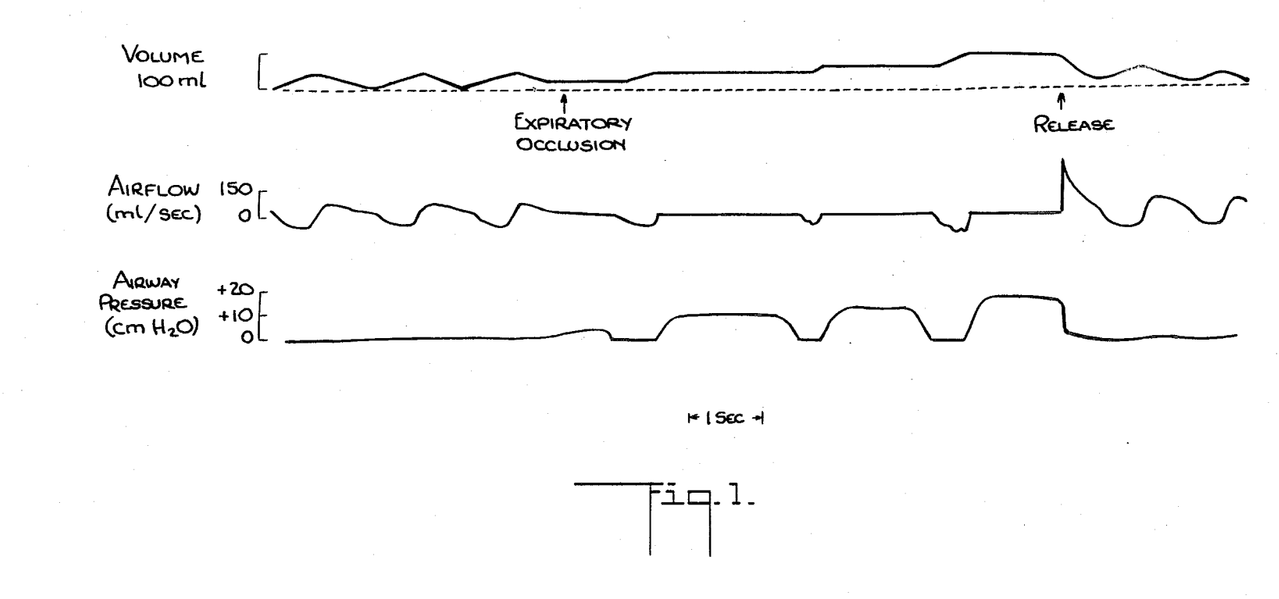

Procedure:

During regular breathing, the expiratory port was silently occluded by manual obstruction either at end-inspiration or during the course of expiration. The expiratory occlusion was then maintained for 3-5 subsequent breaths, permitting the infant to undergo progressive increases in lung volume with each successive unobstructed inspiration via the inspiratory port of the two-way valve (FIG. 1). Thereafter, occlusion of the expiratory valve was suddenly released during the expiratory phase, permitting a passive exhalation. Due to the cumulative increases in lung volume occurring during application of the latter expiratory volume clamp (EVC) maneuver, the accompanying expiratory phases were associated with increasing plateaus in airway pressure, which represented brief periods of apnea attributed to progressive recruitment of the Hering-Breuer reflex. For all the subjects, the maximum increases in airway pressure did not exceed 29 cm H2O, and distinct plateau in pressure were obtained in all the subjects studied (as per FIG. 1), with the exception of three infants. The latter subjects failed to exhibit plateaus in airway pressure due to continuous contraction of their expiratory muscles during each successive expiratory phase, evidenced by a progressive increase in airway pressure throughout the entire course of each occluded expiration. Accordingly, the data from these subjects were not included in the subsequent analyses described infra. In all of the other 22 subjects described herein, the plateau in airway pressure obtained upon initial expiratory occlusion within the tidal volume range lasted between 0.35 and 2.5 sec. With the subsequent occluded expirations, due to progressive recruitment of the Hering-Breuer reflex, the durations of the plateau in airway pressure were increased, and lasted between 0.85 and 7.7 sec. In all the subjects, the EVC maneuver was repeated on at least five separate occasions during regular breathing, which permitted multiple determinations of volume and pressure over an extended lung volume range (details given infra). In this connection, the individual breaths which did not exhibit distinct plateau in airway pressure were not included in the subsequent analysis of the data described below.

Figure 2:
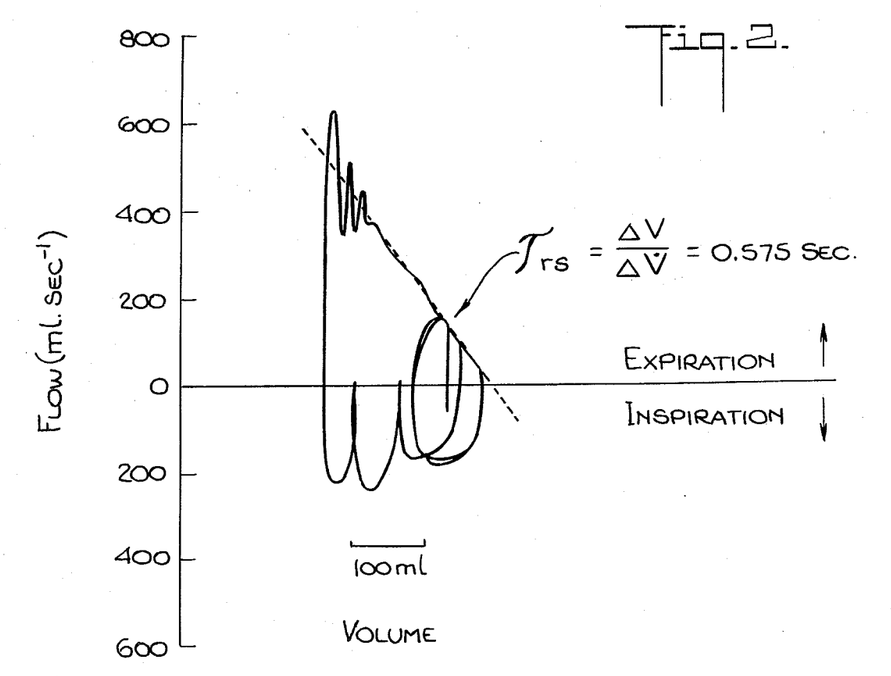
FIG. 2 is a representative trace of flow-volume relationships during tidal breathing using the method described herein.

The cumulative increases in lung volume ($\Delta V$) obtained during the EVC maneuvers were plotted against the corresponding plateau increases in airway pressure (P) to describe the passive volume-pressure ($\Delta V - P$) relationship of the respiratory system. Indices quantifying the curvilinearity and steepness of the latter relationship were then obtained, and an estimate of the net passive compliance of the respiratory system at a transthoracic pressure of 20 cm $H_2O$ (i.e., $C_{\overline{rs}} - 20$) was also derived. These are described under "Results" infra. The passive time constant of the respiratory system was also determined on at least five separate occasions by analyzing the expiratory decay in volume and flow obtained during tidal breathing and/or after release of the expiratory occlusion accompanying the above EVC test. From each exhalation, instantaneous volume was plotted against flow ($V/\dot{V}$) and, in all subjects, the relationship could be closely approximated by a linear function after the first moments of the expiration, as exemplified in FIG. 2. The slope of the $V/\dot{V}$ relationship described the net passive time constant of the respiratory system as described by McIlroy, et al., *J. Appl. Physiol.* 18: 424-427 (1963) which included the added equipment flow resistance. From the above $C_{\overline{rs}} - 20$ and net passive time constant measurements, the corresponding net passive resistance of the respiratory system was derived by dividing the time constant by $C_{\overline{rs}} - 20$. The value of the added equipment flow resistance was then substracted from the net respiratory resistance to obtain both the infant's passive resistance of the respiratory system ($R_{rs}$) and intrinsic passive time constant ($\tau_{rs}$). The measurement of $R_{rs}$ was then expressed in terms of the conductance of the respiratory system ($C_{\overline{rs}}$), i.e., $1/R_{rs}$. Moreover, to the extent that during tidal breathing inspiration typically occurred before the linear flow-volume relationship reached zero flow (see FIG. 2), for each subject we also measured the difference between the dynamic end-expiratory level and the relationship volume of the respiratory system ($V_r$), the latter determined by extrapolation of the linear flow-volume relationship to zero flow, following Kosch, et al., *J. Appl. Physiol.* 57: 1126-1133 (1984); Lesouef, et al., *Am. Rev. Resp. D.s.* 129: 552-556 (1984), Vinegar, et al., *J. Appl. Physiol* 46: 867-87 (1979).

The above measurements of respiratory mechanics were corrected for body weight, and the data was averaged for each subject group. Where appropriate, group comparisons were then conducted using the unpaired Students t-test, with a p value of 0.05 considered statistically significant.

Figure 3:
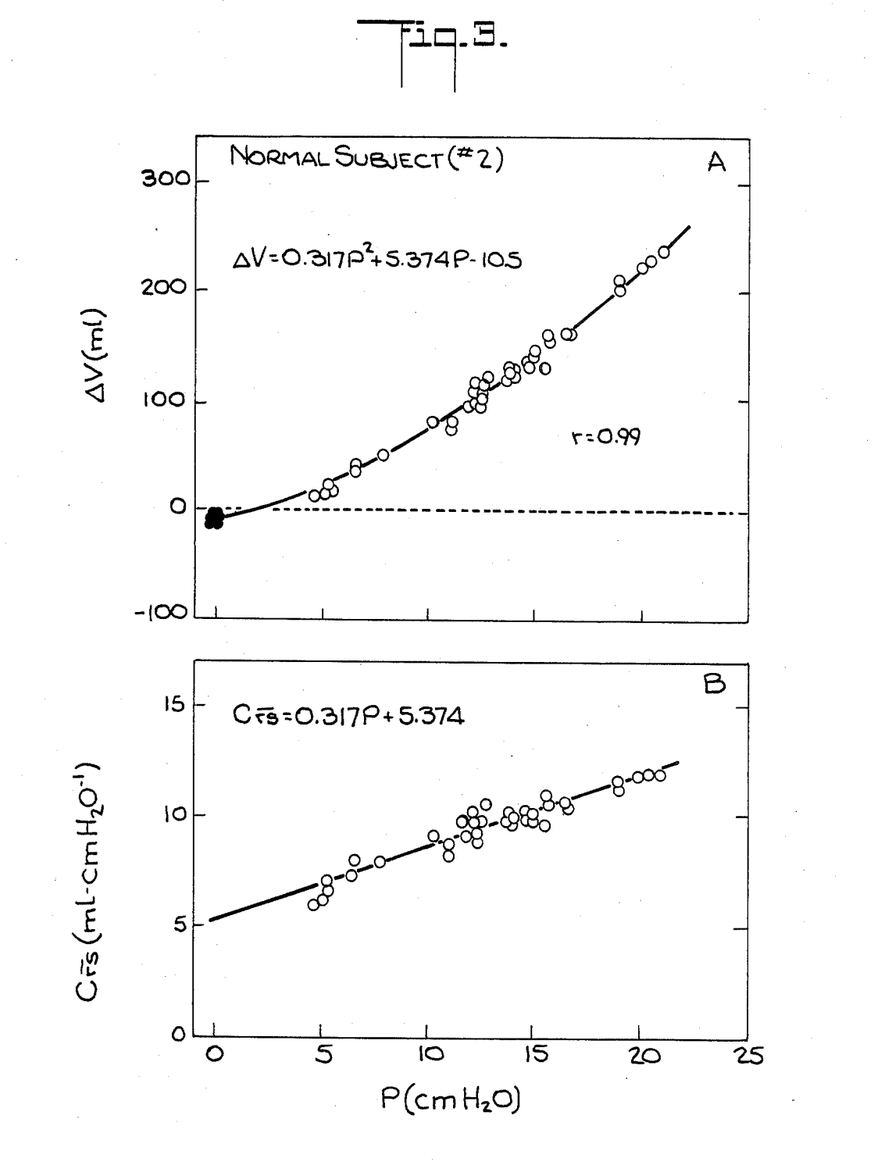
FIG. 3A shows a graph of a typical volume pressure relationship obtained from a normal infant.
FIG. 3B shows relationship between $C_{rs}$ (defined infra), at a given pressure "P", using linear transformation values as set forth in Equation 2 (described infra).

Results:

A representative volume-pressure relationship obtained during repeated EVC testing in a normal infant is depicted in FIG. 3A. Here, V represents the change in lung volume measured relative to the dynamic functional residual capacity (FCR), which is indicated by the dashed line at $\Delta V=0$. The open symbols are the values obtained during the repeated EVC maneuvers initiated at end-inspiration, as well as during expiration at volumes below the tidal level (tidal volume =97.5 ml). On the other hand, the filled symbols are the corresponding measurements of $\Delta V$ at P=O, the latter obtained by extrapolating the linear expiratory flow-volume relationships to zero flow. It can be seen that the data collectively describe a curvilinear relationship which is closely fitted (correlation coefficient; r=0.99) by the following polynomial expression:

$$\Delta V = aP^2 + bP + c \quad (1)$$

wherein the constant c is a negative number which denotes the volume difference between the dynamic FRC and $V_r$, and the constants a and b are indices describing the curvilinearity and steepness of the volume-pressure relationship, respectively. The significance of the latter constants is emphasized when expressing the above polynomial function in terms of its linear transform (i.e., y = ax + b) below:

$$(V-c)/P = aP + b \quad (2)$$

where the expression $(\Delta V-c)/P$ has units of ml/cm $H_2O$ and, accordingly, represents the "point" or "chord" compliance of the respiratory system (i.e., $C_{\overline{rs}}$) pertinent to any given P. Graphically, as illustrated for the same subject in FIG. 3B, the above expression describes a linear function wherein the constant a (in ml/cm $H_2O$) is the slope of the relation and, hence, is a measure of the pressure-related changes in $C_{\overline{rs}}$, whereas the constant b (in ml/cm $H_2O$) is the intercept which represents the $C_{\overline{rs}}$ value obtained at P=O.

Figure 4:
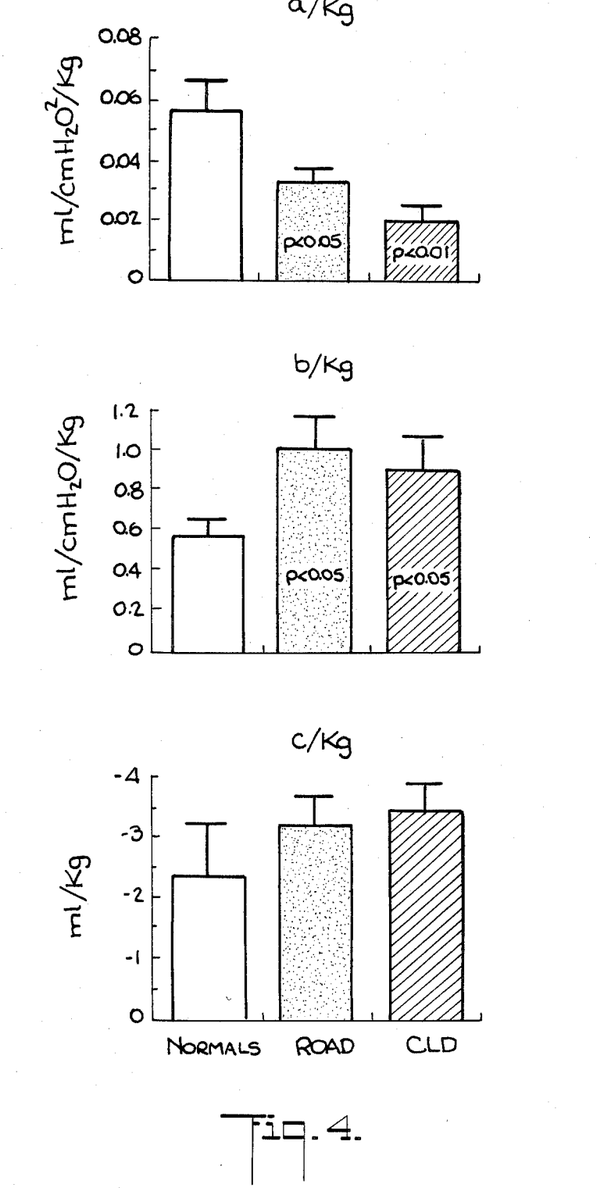
FIG. 4 shows the mean values for the data obtained in the three groups of subjects studied.

The polynomial function given by equation 1 closely approximated the $\Delta V - P$ relationships obtained in all the subjects studied, and the fitted polynomial regressions provided correlation coefficients in excess of 0.98. For each subject, the values for the polynomial constants were corrected to the infant's body weight (in Kg), and the individual weight-specific measurements were then averaged for each subject group. The mean values, including the corresponding ranges of the measurements, are indicated in the following discussion. Here, it will be noted that: (1) all the a/Kg values were positive, implying that the curvilinear $\Delta V - P$ relationships were all oriented convex to the horizontal pressure axis (as per FIG. 3A); and (2) all the c/Kg values were negative, implying that all the subjects breathed from lung volumes above $V_r$. Moreover, as shown in the top panel of FIG. 4, the mean ($\pm$SE) value of a/Kg in the normal infants amounted to 0.057 ($\pm$0.010) ml/cm $H_2O^2$/Kg (open column), and the corresponding mean values in the ROAD (filled column) and CLD infants (hatched column) were significantly reduced at 0.033 ($\pm$0.004) and 0.020 ($\pm$0.004) ml/cm $H_2O^2$/Kg, respectively. In contrast, as illustrated in the middle panel of FIG. 4, the mean ($\pm$SE) value of b/Kg was significantly lower in the normal infants, amounting to 0.576 ($\pm$0.075) ml/cm $H_2O$/Kg, as compared to the values of 1.009 ($\pm$0.163) and 0.900 ($\pm$0.171) ml/cm $H_2O$/Kg obtained in the ROAD and CLD infants, respectively. Based on the considerations noted above these data suggest that, whereas the weight-specific chord compliances ($C_{\overline{rs}}$/Kg) obtaining at P =O (i.e., parameter; b/Kg) were relatively reduced in the normal infants, their corresponding pressure-related changes in $C_{\overline{rs}}$/Kg (i.e., parameter; a/Kg) were relatively more pronounced. Of interest, on the other hand, the mean values of c/Kg did not significantly vary among the different subject groups (FIG. 4; bottom panel) and amounted to $-2.336$ ($\pm 0.851$), $-3.206$ ($\pm 0.431$) and $-3.420$ ($\pm 0.445$) in the normal, ROAD and CLD infants, respectively.

Figure 5:
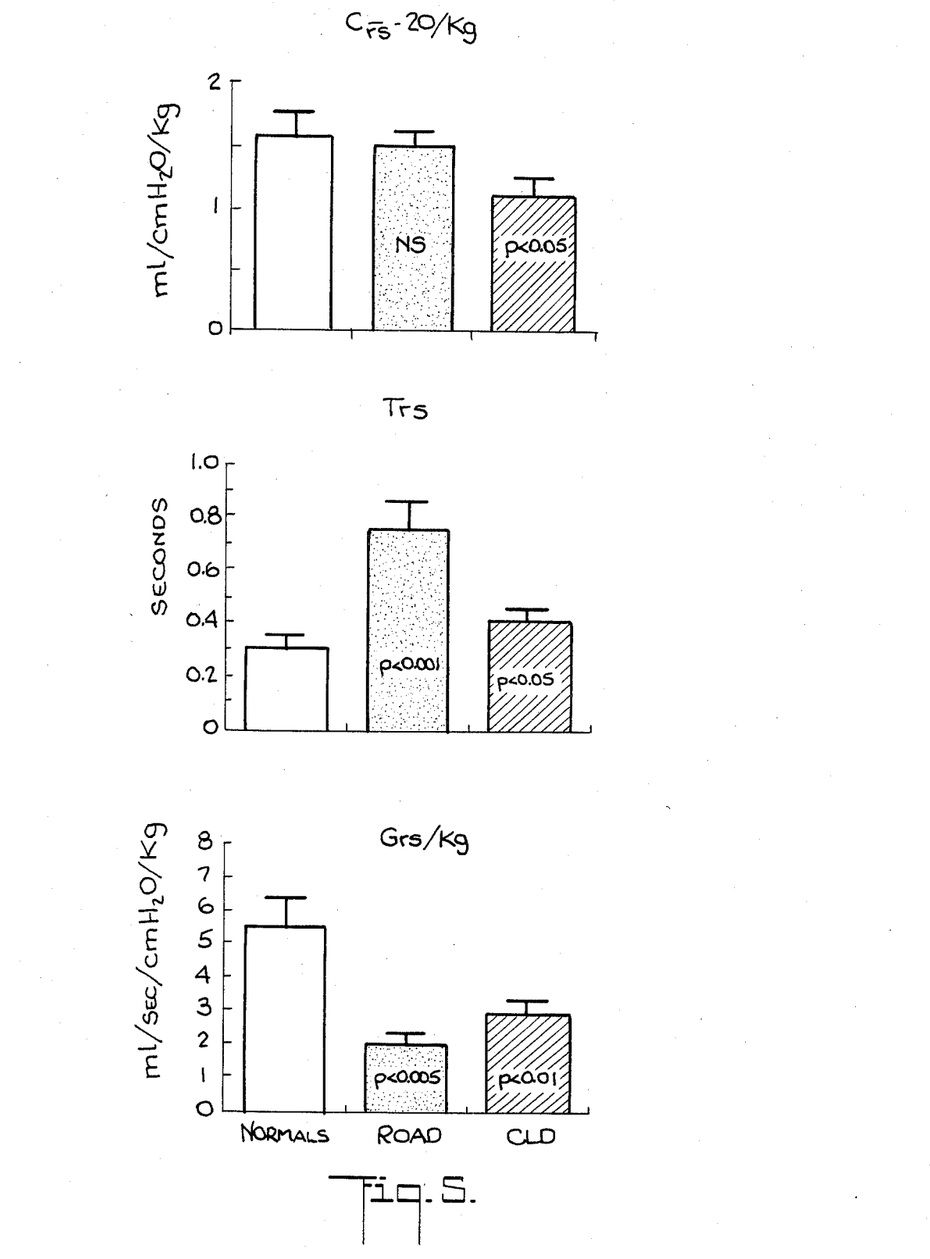
FIG. 5 shows mean valves for $C_{rs}-20/Kg$, $t_{rs}$, and $G_{rs}Kg$ for each group.
Figure 6:
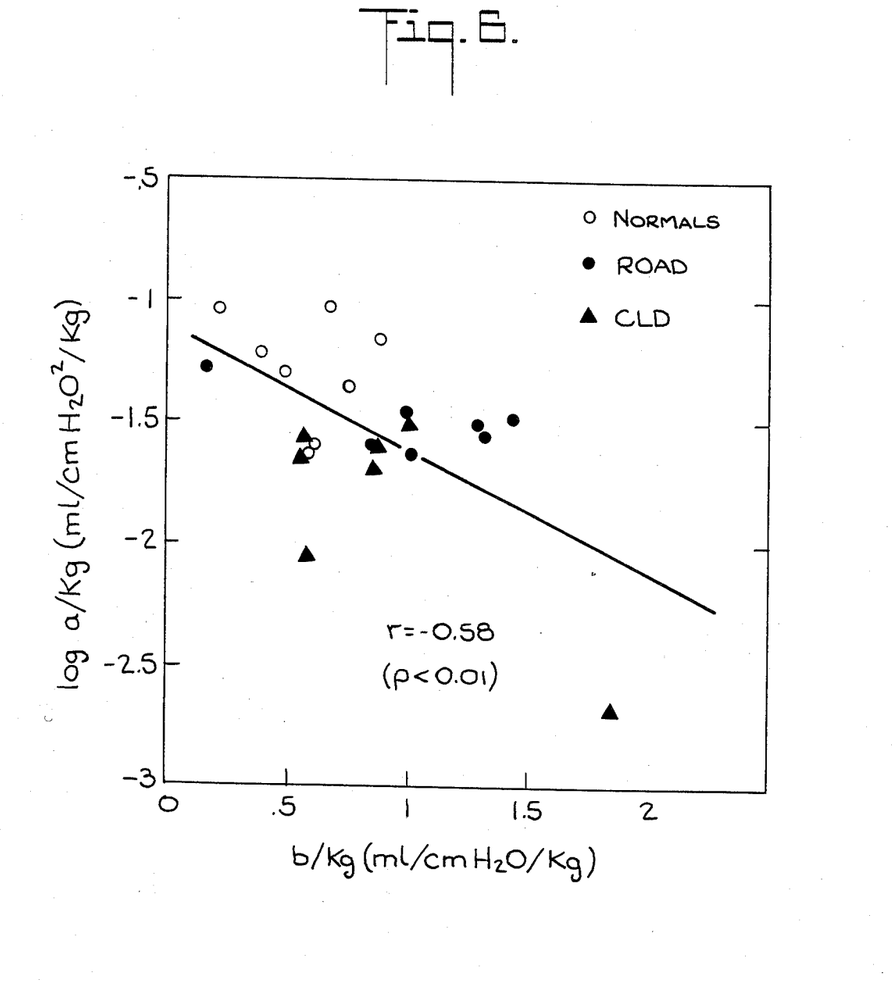
FIG. 6 shows the relationship between individual log a/Kg and b/Kg valves for all subjects. Definition of "a" and "b" are given infra.

In assessing both the inflation and deflation limbs of the passive volume-pressure relationships of the respiratory system in the anesthetized/paralyzed infants, Sharp, et al., *J. Appl. Physiol.* 29: 775–779 (1970) approximated the net total respiratory system compliance in terms of the value obtained at a transthoracic pressure of 20 cm $H_2O$. To the extent that the latter measurement represents a closer estimate of the net passive expiratory (i.e., deflation) compliance of the respiratory system, for each subject we also calculated the $C_{\overline{rs}}$ obtaining at P =20 cm $H_2O$ (i.e., $C_{\overline{rs}-}20$), based on the infant's values for the polynomial constants. The mean and range of the weight-specific values of $C_{rs-}20$ (i.e., $C_{rs-}20$/Kg) are indicated for each subject group in FIG. 5, which also includes the corresponding mean values of $\tau_{rs}$ (in sec) and $C_{\overline{rs}}$/Kg, the latter determination in each subject representing the quotient of $C_{\overline{rs}}$/Kg divided by $\tau_{rs}$. As shown in FIG. 5 (top panel) the mean ($\pm$SE) $C_{\overline{rs}-}20$/Kg value obtained in the normal subjects amounted to 1.606 ($\pm$0.170) ml/cm $H_2O$/Kg, which was not significantly different from the mean value of 1.50 ($\pm$0.117) ml/cm $H_2O$/Kg obtained in the ROAD subjects. In contrast, relative to the normal infants, the CLD patients had a significantly reduced mean $C_{\overline{rs}-}20$/Kg value of 1.129 ($\pm$0.127) ml/cm/$H_2O$/Kg. The corresponding mean ($\pm$SE) $\tau_{rs}$ value in the normal subjects amounted to 0.317 ($\pm$0.031) sec (FIG. 5; middle panel), which was significantly lower than the values of 0.766 ($\pm$0.097) and 0.418 ($\pm$0.038) sec obtained in the ROAD and CLD infants, respectively. Due to the latter differences in $\tau_{rs}$, the accompanying values of $C_{rs}$/Kg were significantly reduced in both patient groups (FIG. 5; lower panel), averaging 2.073 ($\pm$0.19) and 2.829 ($\pm$0.410) ml/sec/cm $H_2O$/Kg in the ROAD and CLD infants, respectively, as compared to the value of 5.495 ($\pm$0.824) ml/sec/cm $H_2O$/Kg obtained in the normal subjects.

While there have been described what are at present considered to be the preferred embodiments of this invention, it will be obvious to one skilled in the art that various changes and modifications may be made therein without departing from the invention, and it is, therefore, aimed to cover all such changes and modifications as fall within the true spirit and scope of the invention.

I claim:

1. A method for measuring respiratory function in a subject comprising:
   (a) covering nose and mouth of said subject with a sealable face mask, said face mask equipped with means connected to a flowmeter, a two way valve with a first port delivering air for inhalation and a second port for removing exhaled air, and connecting means connecting said face mask to a pressure transducer;
   (b) permitting spontaneous breathing by said subject through said first port for a predetermined number of breaths while occluding exhalation of air inhaled by said patient through said first port;

(c) measuring progressive cumulation of inspired volume in the lungs of said subject with said flowmeter and increases in mask pressure with said pressure transducer;

(d) relating said volume cumulation measured with said flowmeter and mask pressure increases measured with said pressure transducer to determine the subject's respiratory compliance;

(e) spontaneously releasing said exhalation occlusion;

(f) measuring flow of exhaled air through said second port following release of said occlusion with said flowmeter;

(g) measuring volume change in said subject's lungs following release of said occlusion;

(h) relating said measured flow and said volume change to determine the time constant of said subject's respiratory system; and, (i) relating the time constant and said respiratory compliance to determine respiratory system resistance in said subject.

2. A method as in claim 1, wherein said subject is an infant.

3. A method as in claim 1, wherein said subject is infirm.

4. A method as in claim 1 wherein said said respiratory system resistance determination is an indication of presence or lack thereof of a respiratory abnormality.

5. A method as in claim 4, wherein said abnormality is a respiratory abnormality characterized by airflow resistance abnormality.

6. A method as in claim 5, wherein said abnormality is asthma.

7. A method as in claim 5, wherein said abnormality is a chronic obstructive pulmonary disease.

8. A method as in claim 4, wherein said abnormality is characterized by parenchymal lung stiffness.

9. A method as in claim 8, wherein said abnormality is emphysema.

10. A method as in claim 8, wherein said abnormality is a restructive lung disease.

* * * * *

UNITED STATES PATENT AND TRADEMARK OFFICE
CERTIFICATE OF CORRECTION

PATENT NO. : 4,802,492

DATED : February 7, 1989

INVENTOR(S) : Michael M. Grunstein

Page 1 of 2

Figure 7:
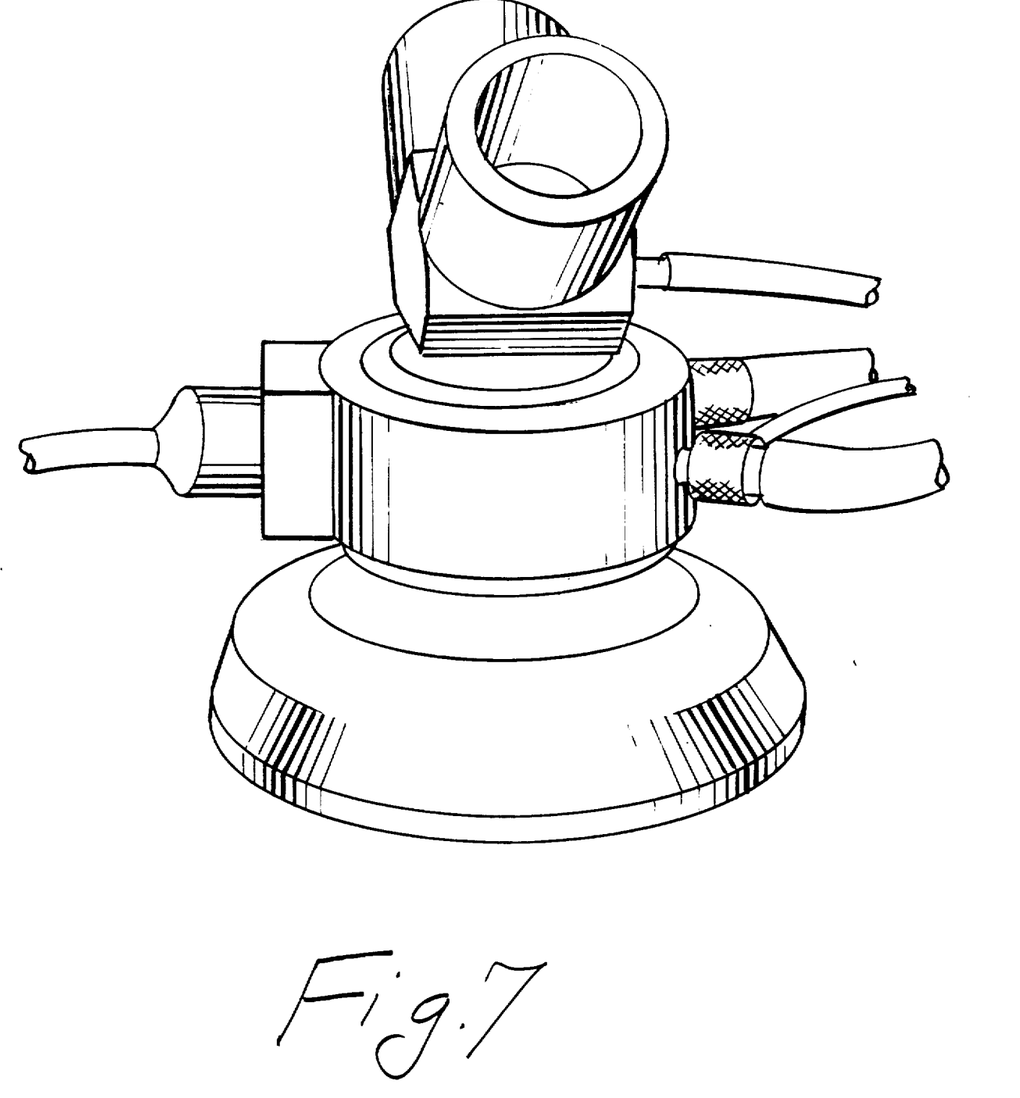
FIG. 7 shows a face mask of the type used in covering the nose and mouth of subjects following the method of this invention.

It is certified that error appears in the above-identified patent and that said Letters Patent is hereby corrected as shown below:

Insert figure 7 as part of Letters Patent as shown on the attached sheet.

Signed and Sealed this

Twenty-sixth Day of September, 1989

Attest:

DONALD J. QUIGG

Attesting Officer

Commissioner of Patents and Trademarks

Fig.7